United States Patent [19]

Gamon

[11] Patent Number: 4,656,295

[45] Date of Patent: Apr. 7, 1987

[54] METHOD OF ISOLATING MACROCYCLIC POLYETHERS

[75] Inventor: Norbert Gamon, Emmerting, Fed. Rep. of Germany

[73] Assignee: Consortium fur Elektrochemische Industrie GmbH, Munich, Fed. Rep. of Germany

[21] Appl. No.: 742,033

[22] Filed: Jun. 6, 1985

[30] Foreign Application Priority Data

Sep. 24, 1984 [DE] Fed. Rep. of Germany ....... 3435017

[51] Int. Cl.$^4$ .......................................... C07D 323/00
[52] U.S. Cl. .................................... 549/352; 540/467
[58] Field of Search .................... 260/239 R; 549/352; 540/467

[56] References Cited

U.S. PATENT DOCUMENTS 4,254,034 3/1981 van Zon .............................. 549/352
4,435,582 3/1984 Krijnen et al. ..................... 549/352

OTHER PUBLICATIONS

Mandolini et al, Synthetic Communications, vol. 9, pp. 851-856 (1979).

*Primary Examiner*—Dolph H. Torrence
*Attorney, Agent, or Firm*—Collard, Roe & Galgano

[57] ABSTRACT

A process for isolating macrocyclic polyethers from open-chained polyglycols in a mixture by extraction with saturated hydrocarbons in the presence of at least 10 percent by weight ethylene glycol based on the weight of the mixture of macrocyclic polyethers and open-chained polyglycols.

3 Claims, No Drawings

METHOD OF ISOLATING MACROCYCLIC POLYETHERS

The present invention relates to a process for isolating macrocyclic polyethers from their mixtures with open-chained polyglycols by extraction with saturated hydrocarbons.

In the synthesis of macrocyclic polyethers, hereinafter also referred to as crown ethers, polyglycols found in the synthesis reaction mixture are primarily open-chained. Such polyglycols are present in the reaction mixture, for example, in the form of incompletely reacted starting compounds or as the resulting products of halides, tosylates and the like having glycol units. The separation of such polyglycols from the crown ethers, which are the desired final product, poses substantial problems because of their similar boiling ranges and solubility properties in known extractants.

The removal of hydroxyl groups-containing compounds from their mixtures with 18-crown-6 by extraction with cold pentane is discussed in SYNTH. COMM. 9, 851 (1979). Under such conditions, however, crown ethers are extracted only very slowly and with unsatisfactory purity.

It is therefore an object of the present invention to provide a process for isolating macrocyclic polyethers from their mixtures with open-chain polyglycols that exhibits a high degree of purity.

To attain the foregoing and related objects, surprisingly, it has been discovered that crown ethers obtained by extraction with saturated hydrocarbons will exhibit a high degree of purity if, at least, 10% by weight ethylene glycol, based on the weight of the mixture of macrocyclic polyethers and open-chained polyglycols, is added to the reaction mixture that is to be subjected to extraction.

Preferably, the amount of ethylene glycol used in the inventive process is from 50 to 200% by weight based on the amount of the mixture of macrocyclic polyethers and open-chained polyglycols.

The macrocyclic polyethers to be isolated from the reaction mixture according to the present invention are particularly those structured with from 5 to 10 ethylene oxide units. The ethylene oxide units may themselves have substituents. Examples of such substituents are, e.g., methyl, ethyl, n-propyl-, n-butyl-, allyl-, crotyl-, prenyl-, phenyl-, benzyl-, methoxymethyl- and ethoxymethyl-, among others.

Individual examples of the crown ethers to be isolated in accordance with the inventive process are, e.g., methyl-18-crown-6, ethyl-18-crown-6, propyl-18-crown-6, 15-crown-5, allyloxymethyl-18-crown-6, 1-aza-18-crown-6, N-methyl-1-aza-18-crown-6, N-allyl-1-aza-18-crown-6, and, in particular, 18-crown-6.

The open-chained polyglycols to be separated by extraction are, in particular, those having the same structural units as the crown ethers to be isolated. Examples of such glycols are, e.g., triethylene glycol, tetraethylene glycol, pentaethylene glycol, hexaethylene glycol, heptaethylene glycol, octaethylene glycol, decaethylene glycol, 1-methyl-tetraethylene glycol, 1-allyl-tetraethylene glycol, 1-phenyl-tetraethylene glycol, diethanolamine, N-methyl-diethanolamine, and N-allyl-diethanolamine.

Examples of the saturated hydrocarbons to be used according to the present invention for extraction are, e.g., straight-chained and branched alkanes, cycloalkanes as well as their mixtures, in particular, n-pentane, n-hexane, n-heptane, n-octane, n-nonane, n-decane, isopentane, isooctane, cyclopentane, cyclohexane and methylcyclohexane, among others.

As a general rule, the extraction temperature is in the range of 20° to 150° C. and, preferably, in the range of 40° to 100° C.

The extraction is carried out by currently known methods for liquid extraction. The extraction may be carried out as a continuous or batch operation. Advantageously, the extraction is carried out countercurrently in a continuous operation. For example, a packed pulsation tower is used, whereby the extractant, e.g., cyclohexane, is admitted at the bottom of the tower; the ethylene glycol at the top of the tower; and the crown ether-containing mixture in the upper third part of the tower.

Following separation of the phases, if need be, and withdrawal of the extractant, the desired crown ether obtained has about 97% purity. In most cases, the crown ethers, isolated by the process according to the invention, will still contain small amounts of ethylene glycol, which, if desired, may be removed, e.g., by azeotropic distillation with toluene.

The process according to the present invention may be used with all syntheses in which crown ether and polyglycols are collected in the reaction mixture. These are, in particular, crown ether syntheses which are carried out in a way similar to the ether synthesis according to Williamson, whereby the initial substances used are polyglycols as well as halides, tosylates and the like having corresponding structural units.

Furthermore, the process according to the invention is suitable for separating those compounds which can be converted into polyglycols, i.e., compounds such as vinyl ethers having corresponding structural units. The vinyl ethers are often collected as by-products in the crown ether synthesis.

In the following examples, the present invention will be more fully described. However, it should be noted that these examples are given only by way of illustration and not of limitation.

EXAMPLE 1

200 kg of a reaction mixture which contained 58% by weight 18-crown-6 and was collected in the synthesis of the crown ether from tetraethylene glycol, 2,2'-dichlorodiethyl ether in the presence of KOH and dimethyl sulfoxide as the solvent, was loaded in a packed pulsation tower (diameter 80 mm; length 6 m) and extracted countercurrently at 80° C. with about 1000 liters cyclohexane. The mixture, which still contained 42% by weight polyglycols (e.g., triethylene glycol, tetraethylene glycol, pentaethylene glycol, hexaethylene glycol and other polyglycol-like compounds), was charged in the upper third part of the tower. 200 kg pure ethylene glycol was admitted at the head of the tower. The extract was collected. The cyclohexane was distilled off and 18-crown-6 was isolated with 98% purity and a yield of 97%.

In an additional purification step, toluene was added and co-extracted ethylene glycol was removed by azeotropic distillation. 18-crown-6 was obtained with a purity of 98.6% (determined by means of gas-chromatography).

EXAMPLE 2

148 g of a mixture of 89 g 18-crown-6 and 59 g polyglycols—which was collected analogous to Example 1 in a crown ether synthesis—was mixed with 152 g ethylene glycol and 900 g cyclohexane and agitated for 30 minutes at 80° C. at high stirrer speed. Subsequently, the mixture was left undisturbed at 80° C. until the phases separated. The specifically lighter phase was separated and the cyclohexane was finally withdrawn. The 18-crown-6 was obtained with 97% purity.

REFERENCE EXAMPLE 1

The procedure specified in Example 2 was repeated, however, with no addition of ethylene glycol.

The purity of the 18-crown-6 came to 86%.

While only several embodiments and examples of the present invention have been shown and described, it is obvious that many changes and modifications may be made thereunto, without departing from the spirit and scope of the invention.

What is claimed is:

1. A process for the isolation of macrocyclic polyethers from open-chained polyglycols in a mixture, comprising the step of:

extracting macrocyclic polyethers from said mixture by extraction with saturated hydrocarbons in the presence of, at least, 10% by weight ethylene glycol based on the weight of the macrocyclic polyethers and open-chained polyglycols in said mixture.

2. The process according to claim 1, wherein the amount of ethylene glycol employed is 50–200% by weight based on the weight of the mixture of macrocyclic polyethers and open-chained polyglycols.

3. The process according to claim 1, wherein said extracting step occurs at a temperature in the range of 40°–100° C.